United States Patent [19]
Stevens

[11] Patent Number: 5,462,560
[45] Date of Patent: Oct. 31, 1995

[54] DOUBLE NEEDLE LIGATURE DEVICE

[75] Inventor: Jon A. Stevens, Hayward, Calif.

[73] Assignee: Tahoe Surgical Instruments

[21] Appl. No.: 134,263

[22] Filed: Oct. 8, 1993

[51] Int. Cl.⁶ .................................................. A61B 17/00
[52] U.S. Cl. .......................... 606/144; 606/139; 606/148; 606/222; 606/169; 606/227
[58] Field of Search ...................... 606/1, 139, 144, 606/145, 147, 148, 150, 167, 222–227, 170, 181, 183–187, 189; 604/173, 267, 268, 272; 112/169, 80.03

[56] References Cited

U.S. PATENT DOCUMENTS

| | | | |
|---|---|---|---|
| 2,670,673 | 3/1954 | Gordon et al. | 604/173 |
| 4,316,469 | 2/1982 | Kapitanov | 606/145 |
| 4,779,616 | 10/1988 | Johnson | 606/148 |

FOREIGN PATENT DOCUMENTS

| | | | |
|---|---|---|---|
| 404226643 | 8/1992 | Japan | 606/222 |
| 0242110 | 11/1925 | United Kingdom | 112/80.03 |
| 0639845 | 7/1950 | United Kingdom | 112/80.03 |

OTHER PUBLICATIONS

Brochure—Ideas for Medicine Inc., Grice Suture Needle.

Primary Examiner—Peter A. Aschenbrenner
Assistant Examiner—Jeffrey A. Schmidt
Attorney, Agent, or Firm—W. Patrick Bengtsson

[57] ABSTRACT

A double needle ligature device for efficiently creating a loop suture for closing wounds, such as trocar wounds. The device preferably includes a double rod-in-needle assembly to ensure that the suture is positively held in place during needle retraction.

9 Claims, 7 Drawing Sheets

DOUBLE NEEDLE LIGATURE DEVICE

FIELD OF THE INVENTION

This invention relates to medical devices used to close surgical wounds, and in particular to a fixed double-needle ligature device particularly useful for creating circumferential ligatures as are needed in, for example, laparoscopic surgery.

BACKGROUND OF THE INVENTION

During laparoscopic surgery, the surgeon often creates a trocar wound; a round hole in tissue that exposes the inside of a body cavity, such as the abdomen. Once the surgery is completed, the trocar wound must be closed. The difficulty lies in creating a loop suture to complete circumferential ligatures around such wounds. More precisely, it is difficult to loop a suture into a body cavity on one side of a wound and get the suture to exit the body cavity on the other side of the wound so the suture ends can be tied to close the trocar wound.

A prior art solution involves using a single needle device, such as the Grice Suture Needle, marketed by Ideas for Medicine, Inc. In this prior art device, the needle is first forced through the tissue while carrying the end of a suture into the body cavity. The needle is then retracted (leaving the end of the suture in the body) and is inserted again on the other side of the wound. A grasper is used to guide the end of the suture to the tip of the reinserted needle. The needle includes a suture holding indentation near its tip in which the suture is secured as the needle is again withdrawn. The suture is then tied to close the wound.

While the prior art procedure is adequate for wound closure, the single+needle procedure includes sequential insertions of the needle into the body cavity, requiring significant surgical skill and manipulation. The sequential process also takes significant time to complete. Further, loss of the suture end from the needle as it is withdrawn is a problem.

It would therefore be advantageous to have a device which could create a loop around a wound, such as a trocar wound, in a shorter time or with less surgical manipulation, in a manner which minimizes the chance of inadvertently losing hold of the suture during needle withdrawal.

SUMMARY OF THE INVENTION

In order to address these concerns, the present invention is directed to a device which includes two needles mounted substantially parallel and separated by a distance greater than the diameter of the wound to be closed. Each needle includes a means for securing the suture to the needle.

In a preferred form of the invention, the ligature device comprises two main parts: a needle assembly and a rod assembly. In this embodiment, the needle assembly is made up of a needle support means (usually a plastic rectangularly shaped bar) for holding needles; first and second hollow needles, each of the needles having a shaft, a proximal end, a distal end, and a sharpened distal tip, and the needles are mounted on the needle support means at their proximal ends. The needles extend substantially parallel to one another from the support means. The needle assembly also includes a first suture support means for slidably supporting a suture, the support means comprising a transverse passage, e.g. a hole, across the shaft of the first needle. The rod assembly of this embodiment includes rod support means for holding rods (again such as a rectangular plastic bar), first and second rods, each of the rods having a shaft, a proximal end, and a distal end, the rods being mounted on the rod support means at their proximal ends. Like the needles, the rods extend substantially parallel to one another from the rod support means. At the distal end of the second rod is positioned a second suture support means for slidably supporting a suture. Preferably this support means is a polymeric or wire filament in the form of a loop.

An important feature of the invention is that the rod assembly is slidably engaged with the needle assembly such that the first and second rods are positioned within the first and second needles and the rod assembly is movable with respect to the needle assembly from a rod extended position to a rod retracted position. When the rod assembly is in the rod extended position, the distal end of the first rod extends past the transverse passage in the first needle. At the same time, this configuration allows the second suture support means (i.e. the loop) to extend past the distal end of the second needle.

By using the structures disclosed herein, the suture loop necessary for closing a trocar type wound can be quickly created by ensuring that the suture is carefully and firmly held within the needles of the device.

BRIEF DESCRIPTION OF THE DRAWINGS

The invention will be better understood by reference to the appended drawings of which.

DETAILED DESCRIPTION OF THE INVENTION

The apparatus of the invention and the method by which it is used is shown in detail in FIGS. 1 through 5.

Figure 1:
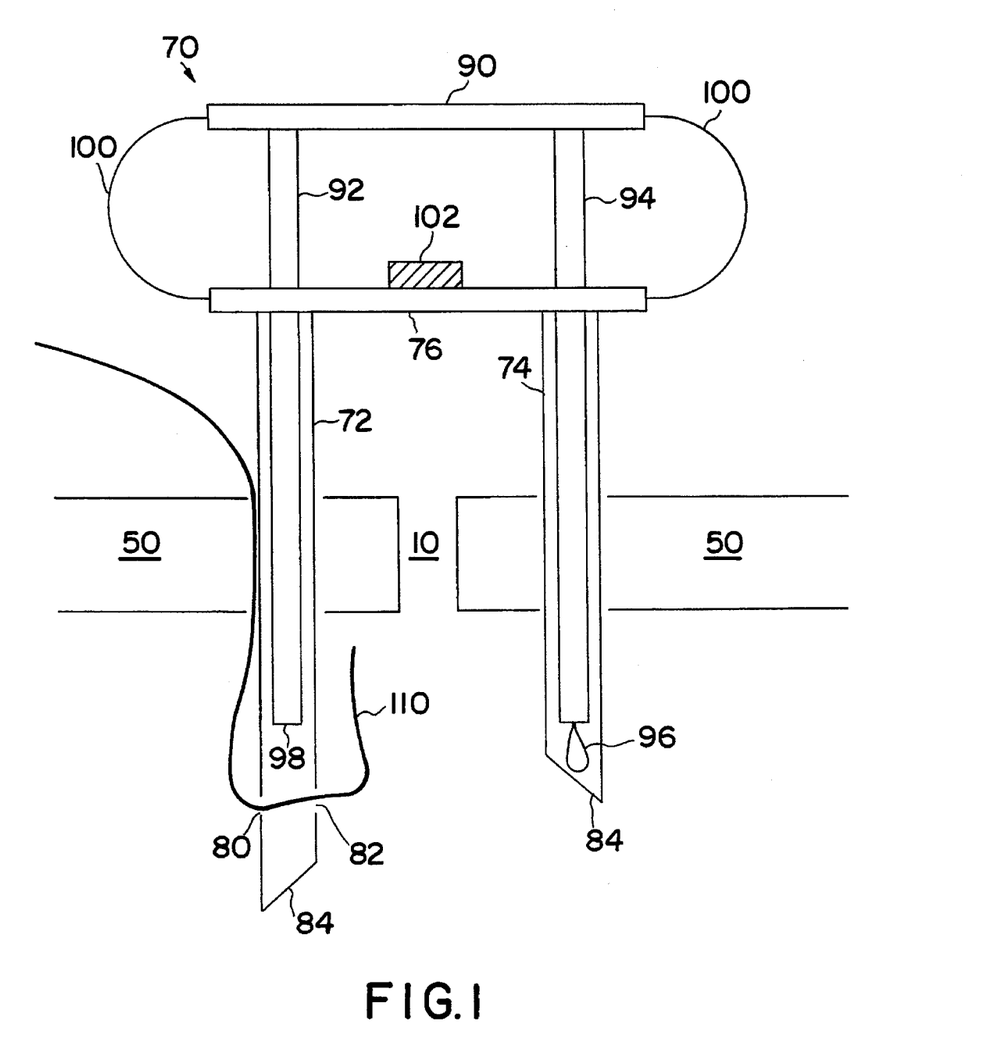
FIG. 1 is a side view of the preferred embodiment of the invention in its relaxed or rod retracted position while inserted into a body cavity.
Figure 2:
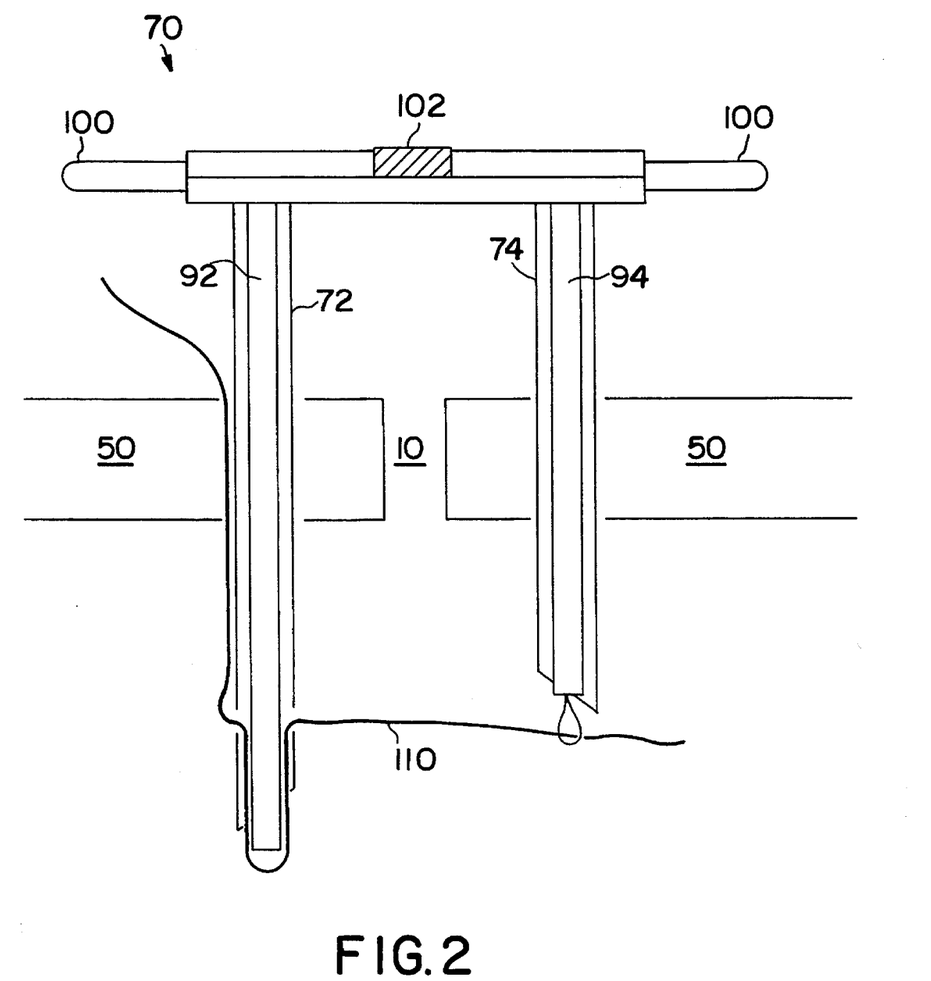
FIG. 2 is a side view of the device of FIG. 1 in a compressed or rod extended position.

The preferred embodiment of the invention is shown in FIG. 1, designated in its entirety by reference number 70. Device 70 includes two hollow needles, suture feed needle 72 and suture retractor needle 74. A needle separation bar (and handle) 76 holds needles 72 and 74 a distance apart and substantially parallel to each other. Feed needle 72 includes aligned holes 80 and 82 near its tip 84. Needle tips 84 on each of needles 72 and 74 have angled cutting ends for easier insertion through tissue. While FIG. 2 shows needle 74 being shorter than the feed needle 72, this is not necessary. However, to date it appears that the uneven length of the needles facilitates the ability to secure the fascia in a proper technical form.

A rod positioner bar 90 secures suture feed rod 92 to retractor rod 94. Rods 92 and 94 are held parallel to each other and are spaced the same distance apart as the needles 72 and 74. Rod 92 inserts into feed needle 72 and rod 94 inserts into loop needle 74.

A suture engaging loop 96 is attached to the end of rod 94. The loop is formed from a filament of metal or plastic, such as polyethylene. Any material which will form the loop and which is inert with respect to tissue can be used.

In order to minimize the degree of manipulation of the device by the surgeon, the degree of insertion of rods 92 and 94 into the needles 72 and 74 can advantageously be controlled by a biasing mechanism 100. Biasing mechanism 100 connects needle handle or bar 76 to bar 90 to provide a flexing motion. In a preferred embodiment, biasing mechanism 100 is formed from plastic or metal tensioners to create a spring tension when forced out of its relaxed state. In its relaxed state, as shown in FIG. 1, biasing mechanism 100 holds bars 76 and 90 apart by such a distance that the end of rod 92 will not pass holes 80 and 82 in needle 72, and loop 96 does not extend from the end of needle 74.

Biasing mechanism 100 is closed by squeezing bars 76 and 90 together, as shown in FIG. 2. When bars 76 and 90 meet, feed rod 92 is forced beyond holes 80 and 82 and loop 96 extends beyond the tip of loop needle 74. Biasing mechanism 100 flexes as bars 76 and 90 are squeezed together. Biasing mechanism 100 supplies a spring pressure when compressed such that when the bars 76 and 90 are released, the device will return to the relaxed state shown in FIG. 1.

Figure 6A:
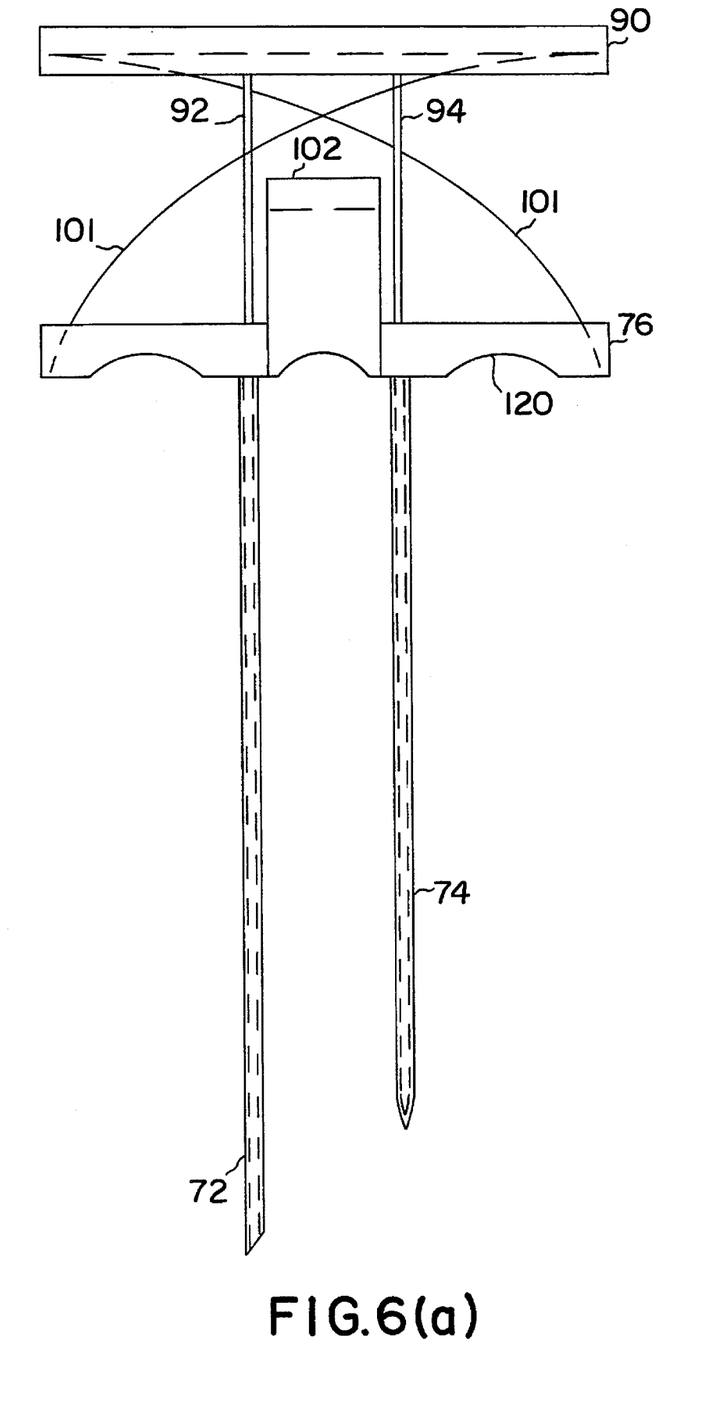
FIGS. 6(a) through 6(c) show an alternative embodiment of the invention.
Figure 6B:
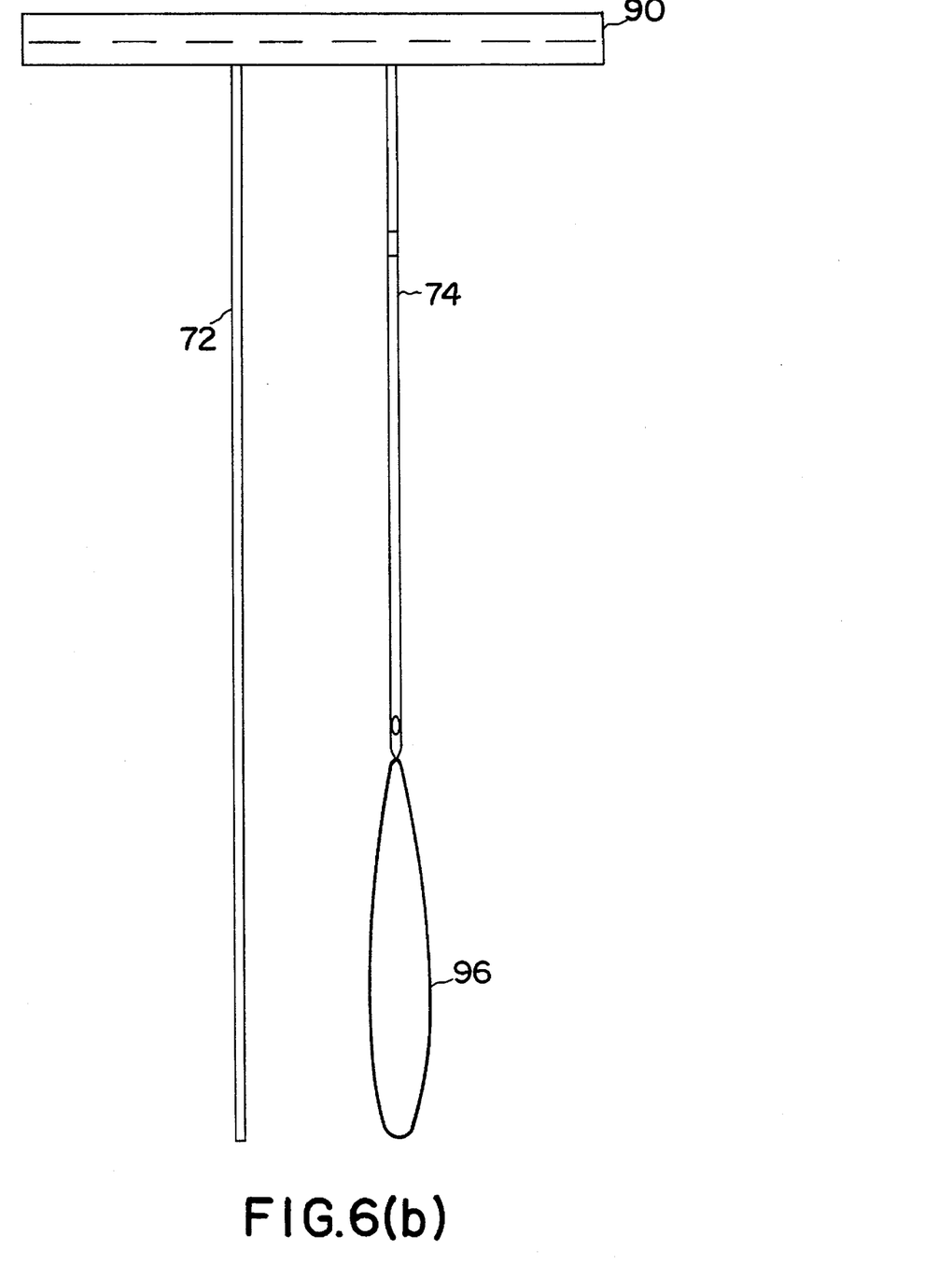
Figure 6C:
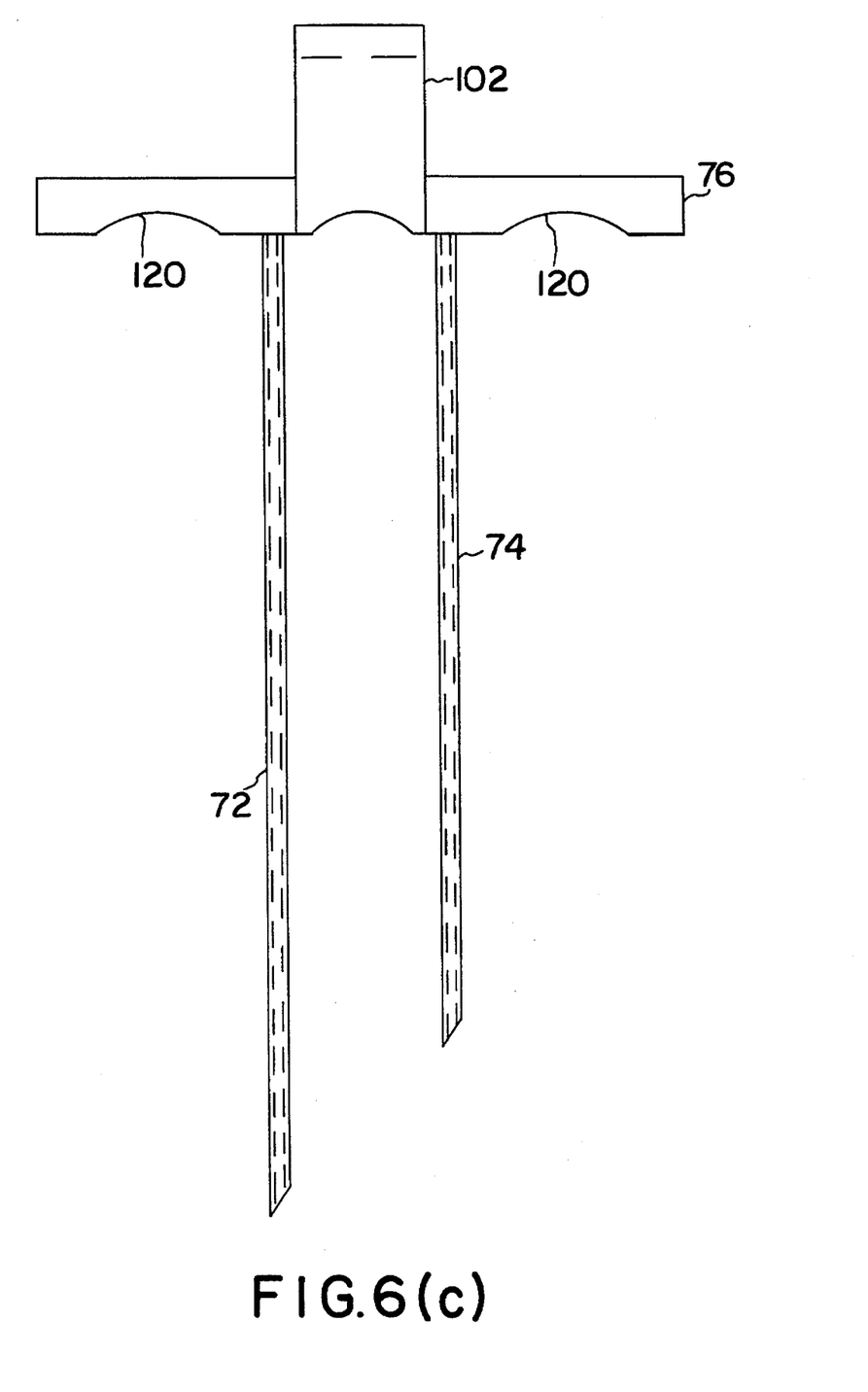

Other types of biasing mechanisms well known to those in the art may be substituted for the mechanism 100. For example, a simple leaf spring mechanism mounted between bars 76 and 90 could be used, as shown in FIGS. 6(a) through 6(c).

Latching mechanism 102 mounted or formed integrally with bar 76 allows bars 76 and 90 to be securely attached together, as shown in FIG. 2. Latch 102 allows the surgeon to lock biasing mechanism 100 in its compressed position. The surgeon may want to let go of the device while it is inserted into the body cavity without the spring force the biasing mechanism 100 returning it to a relaxed position.

Figure 3:
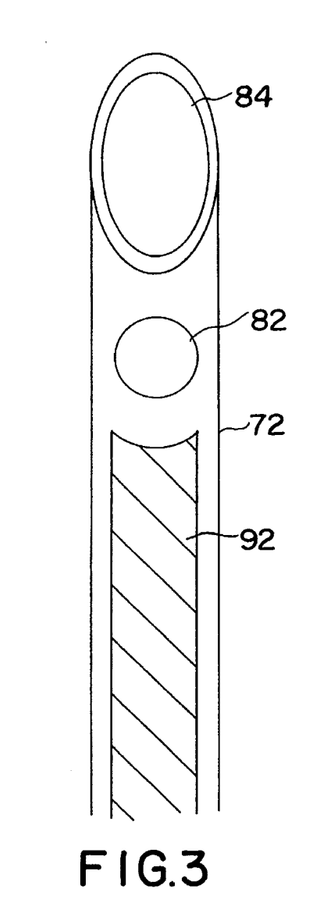
FIG. 3 is a detailed side view showing the feed needle and feed rod.

The end of feed rod 92 is notched, as shown in FIG. 3. Notch 98 is in the same direction as the inline holes 80 and 82 so as to prevent the suture passing through the holes from being cut by feed rod 92 passing holes 80 and 82.

Figure 4A:
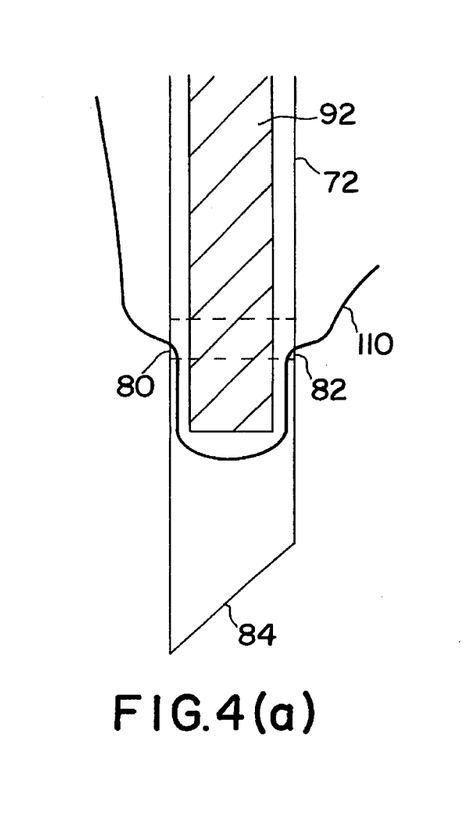
FIGS. 4(a) and 4(b) show the end of the feed needle and feed rod, detailing the primed position of the suture.
Figure 4B:
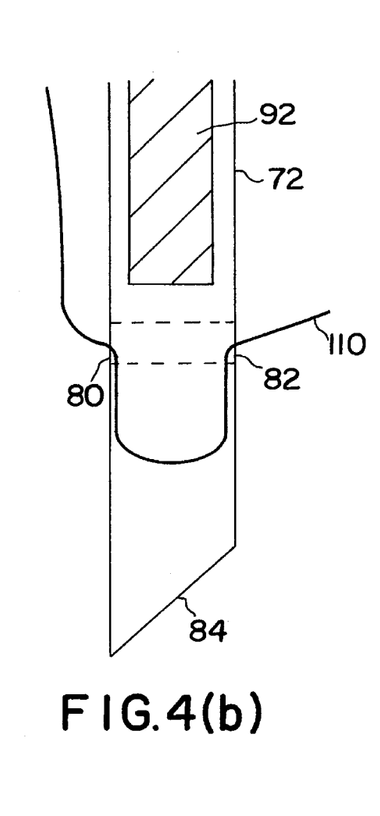
Figure 5:
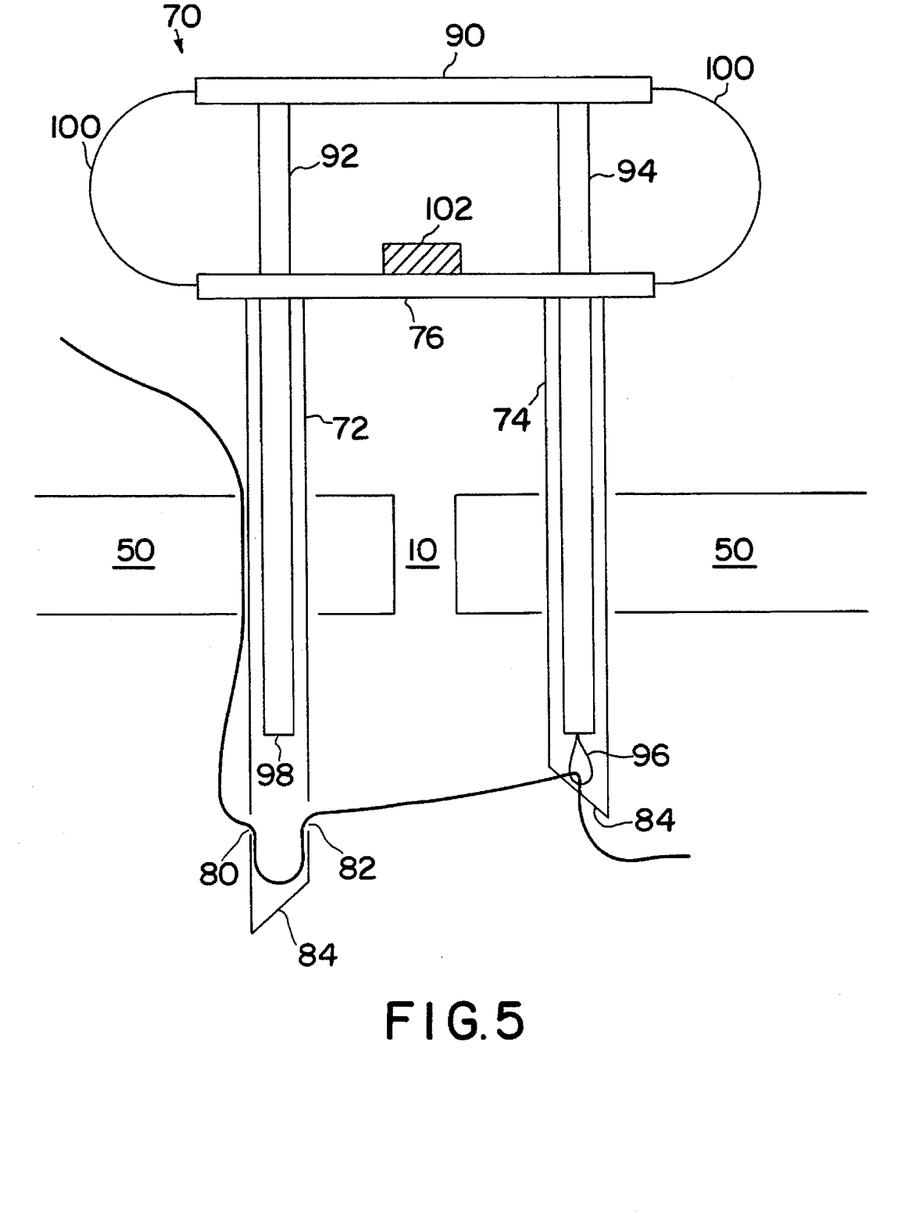
FIG. 5 shows the device during retraction of the suture through the outlet needle.

To close a wound, the strategy shown in FIGS. 4(a), 4(b) and 5 is employed. As shown in FIG. 4(a), a suture end 110 is first threaded through holes 80 and 82. The suture is then "primed" by squeezing bars 76 and 90 together until rod 92 forces the suture slightly past holes 80 and 82. Bars 76 and 90 are then released whereby the suture is left in this "primed" position as shown in FIG. 4(b). In its "primed" position, the suture is securely held such that upon insertion of device 70 into the body cavity, the suture will not slip back through holes 80 and 82.

Device 70 is then inserted through a cavity wall so that the ends of needles 72 and 74 penetrate the wall of the cavity, one on each side of the wound 10, as shown in FIG. 1.

In a preferred method of use, the amount of cavity wall used to close the trocar wound can be advantageously increased by inserting the longer feed needle 72 into the tissue first at approximately a 15° angle. The device is then rotated slightly to a position such that needles 72 and 74 are inserted perpendicular to the skin surface adjacent the wound.

Upon insertion of device 70, suture end 110 will be free inside the body cavity. The surgeon then compresses bar 90 and bar 76 such that loop 96 extends beyond the tip of needle 74, as shown in FIG. 2. Rod 92 passes holes 80 and 82 so as to hold a portion of the suture within feed needle 72 secure. A suture grasper (not shown) is then used to grasp suture end 110 and feed it through loop 96. Bars 90 and 76 are subsequently decompressed to withdraw loop 96 inside loop needle 74, as shown in FIG. 5. Suture end 110 is securely held in place by loop 96. Needles 72 and 74 are then removed from the body, thereby withdrawing the suture held by the loop 96.

As device 70 is removed from the body and the tension increases, the portion of the suture in needle 72 will be pulled taut before the tension is great enough to dislodge the end of the suture from loop 96. Thereafter, the suture will slide freely through holes 80 and 82 to supply a sufficient length of suture to permit removal of the suture from the body.

After the device is removed from the body the surgeon can remove the suture from loop 96, allowing suture ends 96 to be tied together.

While the invention has been described with reference to the closure of trocar wounds arising from laparascopic surgery, those skilled in the art will recognize that the invention will be useful for any procedure requiring ligature of a major vessel or organ. Such procedures would include, for example, a bladder suspension, a uterine neck for a hysterectomy, an apendectomy or a laporascopic bowel resection. An alternative embodiment of the above-described invention is shown in FIGS. 6(a) through 6(c). In this embodiment, a leaf-spring 101 is used to bias bars 76 and 90. Indents 120 are also formed on needle separation bar (handle) 76.

What is claimed is:

1. A ligature device including:
   (1) a needle assembly comprising
       (a) needle support means for holding needles;
       (b) first and second hollow needles, each of said needles having a shaft, a proximal end, a distal end, and a sharpened distal tip, said needles being mounted on said needle support means at their proximal ends and extending substantially parallel to one another from said support means; and
       (c) first suture support means for slidably supporting a suture comprising a transverse passage across said shaft of said first needle; and
   (2) a rod assembly comprising
       (a) rod support means for holding rods;
       (b) first and second rods, each of said rods having a shaft, a proximal end, and a distal end, said rods being mounted on said rod support means at their proximal ends and extending substantially parallel to one another from said rod support means,
       (c) a filament loop, positioned at said distal end of said second rod;
   said rod assembly being slidably engaged with said needle assembly such that said first and second rods are positioned within said first and second needles respectively and said rod assembly is movable with respect to said needle assembly from a rod extended position to a rod retracted position, and, when said rod assembly is in said rod extended position, said distal end of said first rod extends past said transverse passage and said filament loop extends past said distal end of said second needle.

2. A ligature device according to claim 1 further comprising biasing means positioned between said needle support means and said rod support means for urging said needle and rod assemblies toward said rod retracted position.

3. A ligature device according to claim 2 wherein said biasing means comprises a pair of tensioned metal or plastic strips.

4. A ligature device according to claim 1 wherein said needle and rod support means each comprise a rectangularly shaped bar, and said device further comprises biasing means for urging said needle and rod assemblies toward said rod retracted position, said biasing means comprising a pair of tensioned metal or plastic strips extending between said bars.

5. A ligature device according to claim 1 further comprising a releasable lock for locking said needle and rod assemblies together in said rod extended position.

6. A ligature device according to claim 1 wherein said first hollow needle is longer than said second hollow needle.

7. A ligature device including:
(1) a needle assembly comprising first and second hollow needles mounted on a first handle, each of said needles having a shaft, a proximal end, a distal end, said needles being mounted on said first handle at their proximal ends and extending substantially parallel to one another from said first handle, and said first needle having a transverse passage across the shaft thereof; and
(2) a rod assembly comprising first and second rods mounted on a second handle, each of said rods having a shaft, a proximal end, and a distal end, said rods being mounted on said second handle at their proximal ends and extending substantially parallel to one another from said second handle, a loop filament for capturing a suture extending from said distal end of said second rod;

said rod assembly being slidably engaged with said needle assembly such that said first and second rods are positioned within said first and second needles respectively and said rod assembly is movable with respect to said needle assembly from a rod extended position to a rod retracted position, and, when said rod assembly is in said rod extended position, said distal end of said first rod extends past said transverse passage and said loop extends past said distal end of said second needle.

8. A ligature device according to claim 7 further comprising biasing means for urging said needle and rod assemblies toward said rod retracted position.

9. A ligature device according to claim 7 further comprising a releasable lock for locking said needle and rod assemblies together in said rod extended position.

* * * * *